(12) United States Patent
Ishida et al.

(10) Patent No.: US 6,379,659 B1
(45) Date of Patent: Apr. 30, 2002

(54) KERATIN FIBER STRENGTHENING AGENT AND METHOD FOR STRENGTHENING KERATIN FIBER

(75) Inventors: Kenya Ishida; Kazutoshi Sakurai; Miharu Ogura; Tetsuro Yamasaki; Kenichiro Shiroyama, all of Kanagawa (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 09/193,731

(22) Filed: Nov. 17, 1998

(30) Foreign Application Priority Data

Nov. 18, 1997 (JP) ............................... 9-332319

(51) Int. Cl.$^7$ ............................ A61K 7/06; A61K 7/08; A61K 7/075
(52) U.S. Cl. ................. 424/70.1; 424/70.11; 424/70.22; 424/70.28
(58) Field of Search .............................. 424/70.1, 70.11, 424/70.22, 70.28

(56) References Cited

U.S. PATENT DOCUMENTS

| | | | |
|---|---|---|---|
| 5,476,661 A | * | 12/1995 | Pillai et al. .................. 424/401 |
| 5,582,832 A | * | 12/1996 | Pillai et al. .................. 424/401 |
| 5,641,495 A | * | 6/1997 | Jokura et al. ................ 424/401 |
| 5,916,578 A | * | 6/1999 | Kawada et al. |

FOREIGN PATENT DOCUMENTS

| | | |
|---|---|---|
| EP | 0 647 617 A | 4/1995 |
| EP | 0 728 473 A1 | 8/1996 |
| EP | 0 790 053 A1 | 8/1997 |
| EP | 0 875 232 A | 11/1998 |
| FR | 2 679 770 A | 2/1993 |
| WO | WO 98 27958 A | 7/1998 |

OTHER PUBLICATIONS

XP–002123891, Takasago Perfumery Co., Ltd, Preparation of (2S, 3R)–2–aminoalkane–1, 3–diols [(2S,3R)–*dihydrosphingosines*], Jul. 8, 1997, Abstract 127:162 067, Database Chemical Abstracts.

XP–002123892, K. Sakurai et al, "Development and application of an optically active ceramide", vol. 25, No. 10, 1997, pp. 92–98, Japan.

\* cited by examiner

Primary Examiner—Thurman K. Page
Assistant Examiner—S. Howard
(74) Attorney, Agent, or Firm—Sughrue Mion, PLLC (57) ABSTRACT

A keratin fiber strengthening agent comprising 0.001 to 20% by weight of at least one (2S,3R)-2-acylaminoalkane-1,3-diol represented by formula (I):

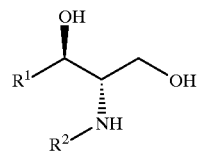

(I)

wherein $R^1$ represents a straight-chain alkyl group having 9 to 17 carbon atoms; and $R^2$ represents an acyl group having 2 to 24 carbon atoms which may contain at least one hydroxy group or unsaturated bond is disclosed. A method for improving physical properties, such as breaking strength, of keratin fiber such as hair comprising applying the keratin fiber strengthening agent to keratin fiber by adhesion, coating or impregnation is also disclosed.

7 Claims, 3 Drawing Sheets

KERATIN FIBER STRENGTHENING AGENT AND METHOD FOR STRENGTHENING KERATIN FIBER

FIELD OF THE INVENTION

This invention relates to an agent to enhance strength of keratin fiber which is hereinafter be referred to as a keratin fiber strengthening agent containing at least one optically active (2S,3R)-2-acyaminoalkane-1,3-diol and a method for improving strength of keratin fiber by applying the keratin fiber strengthening agent to keratin fiber by adhesion, coating or impregnation.

BACKGROUND OF THE INVENTION

Keratin is a body component such as hair, horn, nail, scale or feather which covers the outermost part of a body and is originally derived from the epidermis. Morphologically, it can be classified into a fibrous type and amorphous type. The former type is called keratin fiber and it includes hair, eyebrows and eyelashes and animal hair such as wool and dog hair.

The primary function of keratin is to protect the body of a higher animal, particularly an animal higher than a batrachian, from the outside attack. Another function of keratin is to keep the appearance of an individual body beautiful and this function has a close relation with retention and improvement of the strength of keratin. Accordingly, it is important to maintain and reinforce the strength of keratin or improve the strength of damaged keratin.

Keratin exists in the outermost part of the body so that it tends to be exposed to severe attack from the outer world. Particularly keratin fiber is susceptible to the outer influence.

For example, the physical factors in the natural world such as friction, rain, dirt, dust or ultraviolet rays and microbiological factors such as dandruff bacteria damage keratin fiber of hair. In addition, thermal or chemical irritation due to permanent waving and degreasing due to hair washing with a solvent or detergent have recently increased the frequency of hair being damaged.

Thermal and chemical irritation of permanent waving or degreasing caused by washing with a solvent or detergent decreases the tensional strength of keratin fiber owing to the damage of protein filament. For example, hair tends to reduce tensional strength according to the frequency of permanent waving. It has been reported that the strength of hair is reduced to about half of the untreated hair at the tenth treatment.

In addition, the hair so damaged and having a reduced strength loses its gloss. Such a reduction in the strength produces broken hair or spilt hair, thereby deteriorating the appearance, which causes a cosmetic problem.

It is therefore cosmetically significant to maintain and increase the strength of keratin fiber and improve the strength of damaged keratin fiber.

Keratin is mainly composed of keratin protein (keratin in a narrow sense) which is an insoluble, stable protein containing much cystine and having many disulfide bonds.

Keratin fiber has a definite structure in which protein filament of alfa keratin forms helix coils in the presence of an adhesive. This adhesive has an important role. In addition to keratin protein, keratin fiber contains a number of components. Among them, a water soluble component such as amino acid is presumed to provide keratin fiber with wetness, serving as a humidity retaining component. As an oil component, a ceramide is contained much in keratin fiber.

The ceramide is also a main component of stratum corneum lipid which binds stratum corneum of human skin and is known to play an important role as a skin barrier.

The ceramide extracted from a naturally-occurring substance has an optically active (2S,3R)-2-acylaminoalkane-1,3-diol structure. A 2-acylaminoalkane-1,3-diol has four stereoisomers (diastereomers). Among them, only the stereoisomer having a (2S,3R) configuration exists in nature. It has so far been difficult to prepare the same 2-acylaminoalkane-1,3-diol having a (2S,3R)-configuration as the naturally-occurring one except for preparing it by extraction of a ceramide from a naturally-occurring substance.

Since a ceramide extracted from an animal or plant in nature is a mixture of many ceramide components and it is markedly expensive, studies on the effect of an optically active (2S,3R)-2-acylaminoalkane-1,3-diol, which is a pure substance and at the same time has the single steric structure as that of the naturally-occurring substance, on the keratin fiber have not been reported yet.

As a substitute for the naturally-occurring substance, synthesized is a diastereomer mixture of racemic 2-acylaminoalkane-1,3-diols, that is, a mixture wherein (2S, 3R):(2R,3S) is 1:1 and (2S,3S):(2R,3R) is 1:1 (with the proviso that (2S,3R)+(2R,3S):(2S,3S)+(2R,3R) tend to be unequal) (said mixture will hereinafter be referred to as "racemic ceramide"). It is commercially available under the trade name of "CERAMIDE II" (Quest Inc.) and the use of a composition obtained by mixing it with at least one cosmetically acceptable raw material has been proposed with a view to improving the rough skin or protecting the hair.

It is known (JP-A-4-327563) (the term "JP-A" as used herein means an "unexamined published Japanese patent application") that a composition available by using a "racemic ceramide" is effective for preventing hair from losing moisture. It is also known that a composition containing a "racemic ceramide" imparts satisfactory shape retaining properties to hair (JP-A-7-30046). Further, JPA-8-245337 proposes a method for treating keratin fiber of the skin or hair, etc., which comprises applying a composition containing a "racemic ceramide" to the skin or hair and, optionally, rinsing with water. These reports however do not include a description concerning an increase in the strength of keratin fiber. Even by the studies of the present inventors, no effect for improving keratin fiber was found from the "racemic ceramide" as described later in Examples.

The strength of protein fiber can be determined by measuring a load required for cutting keratin fiber in tension (breaking strength). Permanent-waved hair tends to have a reduced breaking strength. It has been reported that compared with untreated hair, the strength of hair is reduced to about half when permed 10 times. Many compounds have been developed for restoration of such damaged hair. Reported substances effective in restoring damaged hair include cationic hydrolysis products of protein and isoprene glycol (see *Hifu to biyo*, 29(3), 5027(1997)). These reports however do not include a description about an improvement in the strength of keratin fiber.

SUMMARY OF THE INVENTION

An object of the present invention is to provide a novel keratin fiber strengthening agent which can improve physical properties of keratin fiber, such as breaking strength.

The present inventors have proceeded with an extensive study. As a result, it has been found that a composition comprising a compound represented by the formula (I) and a cosmetically acceptable raw material (base) such as oil components, lipids, sterols, lower alcohols, polyols, surfactants and other components brings about a marked improvement in the breaking strength of hair damaged by a permanent wave, treatment with an organic solvent, etc.

That is, it has been found that the composition of the present invention increases breaking strength of keratin fiber and, when applied to hair, produces effects in preventing hair splits or breaks and is curative of hair damage so that it is useful as a product of a keratin fiber strengthening agent. The present invention has been completed based on this finding and successive studies.

The present invention provides:

1) A keratin fiber reinforcing agent comprising 0.001 to 20% by weight of at least one (2S,3R)-2-acylaminoalkane-1,3-diol represented by the following formula (I):

(I)

wherein $R^1$ represents a straight-chain alkyl group having 9 to 17 carbon atoms and $R^2$ represents an acyl group having 2 to 24 carbon atoms which may contain at least one hydroxyl group or unsaturated bond.

2) The keratin fiber strengthening agent according to 1) above, wherein in the formula (I), $R^1$ represents a straight-chain alkyl group having 9 to 17 carbon atoms and $R^2$ represents a saturated acyl group having 2 to 24 carbon atoms.

3) The keratin fiber strengthening agent according to 1) above, wherein in the formula (I), $R^1$ represents a $C_{13}H_{27}$, $C_{15}H_{31}$ or $C_{17}H_{35}$ group and $R^2$ represents an acyl group represented by any one of the following formulas (II) to (VII):

(II)

(III)

(IV)

(V)

(VI)

(VII)

wherein $R^3$ represents a hydrogen atom or a saturated alkyl group having 1 to 21 carbon atoms.

4) The keratin fiber strengthening agent according to 3) above, wherein in the formulas (II) to (VII), $R^3$ represents a $C_{11}H_{23}$, $C_{13}H_{27}$, $C_{17}H_{35}$ or $C_{15}H_{31}$ group.

5) The keratin fiber strengthening agent according to 1) above, wherein $R^2$ represents an acetyl, oleoyl, linoleoyl or linolenoyl group.

6) The keratin fiber strengthening agent according to any one of 1) to 5) above, which further comprises a cosmetically acceptable raw material.

7) The keratin fiber strengthening agent according to any one of 1) to 5) above, which comprises 0.005 to 5% by weight of at least one compound represented by the formula (I).

8) The keratin fiber strengthening agent according to 6) above, wherein the cosmetically acceptable raw material comprises at least one material selected from the group consisting of oil components, lipids, sterols, lower or polyhydric alcohols and surfactants.

9) A method for improving the strength of keratin fiber, which comprises applying the keratin fiber strengthening agent according to any one of 1) to 8) above to keratin fiber by adhesion, coating or impregnation.

DETAILED DESCRIPTION OF THE INVENTION

The present invention will hereinafter be described more specifically.

Although there is no particular limitation imposed on the process for preparing an optically active (2S,3R)-2-acylaminoalkane-1,3-diol of the formula (I) in the present invention that has a stereospecific (2S,3R)-configuration, a process for preparing it by acylating a (2S,3R)-2-aminoalkane-1,3-diol, which is available in accordance with the process as described in JP-A-6-80617, with an appropriate fatty acid or derivative thereof can be given as an example.

(T)—Binap: 2,2'-bis(di-p-tolyphosphino)(-1,1'-binaphthyl)

The fatty acid or derivative thereof used here is a compound represented by the following formula (VIII):

$$R^2-OH \qquad (VIII)$$

wherein $R^2$ represents an acyl group having 2 to 24 carbon atoms which may contain at least one hydroxyl group or unsaturated bond, or a group represented any one of the following formulas (II) to (VII):

wherein $R^3$ represents a hydrogen atom or a saturated alkyl group having 1 to 21 carbon atoms, or $R^2$ represents an acetyl, oleoyl or linoleoyl group.

Specific examples of the fatty acid or derivative thereof include, but not limited to, those exemplified in 1) to 4) below:

1) Saturated fatty acids such as acetic acid, propionic acid, butanoic acid, pentanoic acid, hexanoic acid, octanoic acid, decanoic acid, dodecanoic acid, tetradecanoic acid, hexadecanoic acid, icosanoic acid, docosanoic acid and tetracosanoic acid;

2)-2-Hydroxy acids such as glycolic acid, lactic acid, (S)-lactic acid, (R)-lactic acid, 2-hydroxybutanoic acid, (S)-2-hydroxybutanoic acid, (R)-2-hydroxybutanoic acid, 2-hydroxyhexanoic acid, (S)-2-hydroxyhexanoic acid, (R)-2-hydroxyhexanoic acid, 2-hydroxyoctanoic acid, (S)-2-hydroxyoctanoic acid, (R)-2-hydroxyoctanoic acid, 2-hydroxydecanoic acid, (S)-2-hydroxydecanoic acid, (R)-2-hydroxydecanoic acid, 2-hydroxydodecanoic acid, (S)-2-hydroxydodecanoic acid, (R)-2-hydroxydodecanoic acid, 2-hydroxytetradecanoic acid (which may be referred to as "2-hydroxymyristic acid"), (S)-2-hydroxytetradecanoic acid, (R)-2-hydroxytetradecanoic acid, 2-hydroxyhexadecanoic acid (which may be referred to as "2-hydroxypalmitic acid"), (S)-2-hydroxyhexadecanoic acid, (R)-2-hydroxy hexadecanoic acid, 2-hydroxyoctadecanoic acid (which may be referred to as "2-hydroxystearic acid"), (S)-2-hydroxyoctadecanoic acid, (R)-2-hydroxyoctadecanoic acid, 2-hydroxyicosanoic acid (which may be referred to as "2-hydroxyarachidic acid"), (S)-2-hydroxyicosanoic acid, (R)-2-hydroxyicosanoic acid, 2-hydroxytetracosanoic acid, (S)-2-hydroxytetracosanoic acid and (R)-2-hydroxytetracosanoic acid, 3)-3-Hydroxypropionic acid, 3-hydroxybutanoic acid, (S)-3-hydroxybutanoic acid, (R)-3-hydroxybutanoic acid, 3-hydroxyhexanoic acid, (S)-3-hydroxyhexanoic acid, (R)-3-hydroxyhexanoic acid, 3-hydroxyoctanoic acid, (S)-3-hydroxyoctanoic acid, (R)-3-hydroxyoctanoic acid, 3-hydroxydecanoic acid, (S)-3-hydroxydecanoic acid, (R)-3-hydroxydecanoic acid, 3-hydroxydodecanoic acid, (S)-3-hydroxydodecanoic acid, (R)-3-hydroxydodecanoic acid, 3-hydroxytetradecanoic acid, (S)-3-hydroxytetradecanoic acid, (R)-3-hydroxytetradecanoic acid, 3-hydroxyhexadecanoic acid, (S)-3-hydroxyhexadecanoic acid, (R)-3-hydroxyhexadecanoic acid, 3-hydroxyoctadecanoic acid, (S)-3-hydroxyoctadecanoic acid and (R)-3-hydroxyoctadecanoic acid, and 4) unsaturated fatty acids such as oleic acid, linoleic acid, linoleinic acid and palmitoleic acid.

There is no particular limitation imposed on the process for acylating a (2S,3R)-2-aminoalkane-1,3-diol with the fatty acid of the formula (VIII) or derivative thereof. An ordinary acylation process can be employed. Described specifically, the compound of the formula (I) can be prepared by subjecting a fatty acid of the formula (VIII) or derivative thereof and a (2S,3R)-2-aminoalkane-1,3-diol to dehydrating reaction in the presence or absence of a catalyst under heating conditions. As the catalyst usable upon the dehydrating reaction, an acid catalyst can be mentioned as an example, but it is not necessary to add a catalyst when the reaction is effected at high temperature.

The compound of the formula (I) can also be prepared by introducing a fatty acid of the formula (VIII) or derivative thereof into an acylating agent and then reacting a (2S,3R)-2-aminoalkane-1,3-diol with the resulting acylating agent.

Examples of the acylating agent represented here include acid halides, acid anhydrides, mixed acid anhydrides and esters, para-nitrophenyl ester and N-hydroxysuccinimide ester of the fatty acid of the formula (VIII) or derivative thereof.

The compound of the formula (I) can also be obtained by converting a fatty acid of the formula (VIII) or derivative thereof into an acylating agent in situ in the reaction mixture by using a dehydrating agent and then reacting a (2S,3R)-2-aminoalkane-1,3-diol with the resulting acylating agent without isolation. Examples of the dehydrating agent applied here include carbodiimides, carbonyl diimidazole and triphenylphosphine-2-mercaptopyridine disulfide.

In the acylation of a (2S,3R)-2-aminoalkane-1,3-diol with a fatty acid of the formula (VIII) or derivative thereof, the acylation can be effected without protecting the hydroxyl group or acylation is effected after protecting the hydroxyl group with an appropriate protecting group as needed and removing the protecting group after the completion of the reaction, whereby a desired amide compound can be obtained.

As the optically active (2S,3R)-2-acylaminoalkane-1,3-diol which is used in the present invention and has a stereospecific (2S,3R)-configuration, compounds as described below can be mentioned. Specific examples of the compound of the formula (I) wherein $R^1$ represents a group having 15 carbon atoms include, but not limited to:

1) (2S,3R)-2-acetylaminooctadecane-1,3-diol, (2S,3R)-2-butanoylaminooctadecane-1,3-(2S, 3R)-2-pentanoylaminooctadecane-1,3-diol, (2S,3R)-2-hexanoylaminooctadecane-1,3-diol, (2S,3R)-2-octanoylaminooctadecane-1,3-diol, (2S,3R)-2-decanoylaminooctadecane-1,3-diol, (2S,3R)-2-dodecanoylaminooctadecane-1,3-diol, (2S,3R)-2-tetradecanoylaminooctadecane-1,3-diol, (2S,3R)-2-hexadecanoylaminooctadecane-1,3-diol, (2S,3R)-2-octadecanoylaminooctadecane-1,3-diol, (2S,3R)-2-icosadecanoylaminooctadecane-1,3-diol, (2S,3R)-2-docosanoylaminooctadecane-1,3-diol and (2S,3R)-2-tetracosanoylaminooctadecane-1,3-diol, 2) (2S,3R)-2-glycolylaminooctadecane-1,3-diol, (2S,3R)-2-lactylaminooctadecane-1,3-diol, (2S, 3R)-2-{(S)-lactyl}aminooctadecane-1,3-diol, (2S,3R)-2-{(R)-lactyl}aminooctadecane-1,3-diol, (2S,3R)-2-(2-hydroxybutanoyl)aminooctadecane-1,3-diol, (2S,3R)-2-{(S)-2-hydroxybutanoyl}aminooctadecane-1,3-diol, (2S, 3R)-2-{(R)-2-hydroxybutanoyl}aminooctadecane-1,3-diol, (2S,3R)-2-(2-hydroxypentanoyl)aminooctadecane-1,3-diol, (2S,3R)-2-{(S)-2-hydroxypentanoyl}aminooctadecane-1,3-diol, (2S,3R)-2-{(R)-2-hydroxypentanoyl}aminooctadecane-1,3-diol, (2S,3R)-2-(2-hydrohexanoyl)aminooctadecane-1,3-diol, (2S,3R)-2-{(S)-2-hydroxyhexanoyl}aminooctadecane-1,3-diol, (2S, 3R)-2-{(R)-2-hydroxyhexanoyl}aminooctadecane-1,3-diol, (2S,3R)-2-(2-hydroxyoctanoyl)aminooctadecane-1,3-diol, (2S,3R)-2-{(S)-2-hydroxyoctanoyl}aminooctadecane-1,3-diol, (2S,3R)-2-{(R)-2-hydroxyoctanoyl}aminooctadecane-1,3-diol, (2S,3R)-2-(2-hydroxydecanoyl)aminooctadecane-1,3-diol, (2S,3R)-2-{(S)-2-hydroxydecanoyl}aminooctadecane-1,3-diol, (2S,3R)-2-{(R)-2-hydroxydecanoyl}aminooctadecane-1,3-diol, (2S,3R)-2-(2-hydroxydodecanoyl)aminooctadecane-1,3-diol, (2S,3R)-2-{(S)-2-hydroxydodecanoyl}aminooctadecane-1,3-diol, (2S,3R)-2-{(R)-2-hydroxydodecanoyl}aminooctadecane-1,3-diol, (2S,3R)-2-(2-hydroxytetradecanoyl) aminooctadecane-1,3-diol, (2S,3R)-2-{(S)-2-hydroxytetradecanoyl}aminooctadecane-1,3-diol, (2S,3R)-2-{(R)-2-hydroxytetradecanoyl}aminooctadecane-1,3-diol, (2S,3R)-2-(2-hydroxyhexadecanoyl)aminooctadecane-1,3-diol, (2S, 3R)-2-{(S)-2-hydroxyhexadecanoyl}aminooctadecane-1,3-diol, (2S,3R)-2-{(R)-2-hydroxyhexadecanoyl}aminooctadecane-1,3-diol, (2S,3R)-2-(2-hydroxyoctadecanoyl)aminooctadecane-1,3-diol, (2S, 3R)-2-{(S)-2-hydroxyoctadecanoyl}aminooctadecane-1,3-diol, (2S,3R)-2-{(R)-2-hydroxyoctadecanoyl}aminooctadecane-1,3-diol, (2S,3R)-2-(2-hydroxyicosanoyl)aminooctadecane-1,3-diol, (2S,3R)-2-{(S)-2-hydroxyicosanoyl}aminooctadecane-1,3-diol, (2S, 3R)-2-{(R)-2-hydroxyicosanoyl}aminooctadecane-1,3-diol, (2S,3R)-2-(2-hydroxytetracosanoyl)aminooctadecane-1,3-diol, (2S,3R)-2-{(S)-2-hydroxytetracosanoyl}aminooctadecane-1,3-diol, and (2S, 3R)-2-{(R)-2-hydroxytetracosanoyl}aminooctadecane-1,3-diol, 3) (2S,3R)-2-(3-hydroxypropanoyl)aminooctadecane-1,3-diol, (2S,3R)-2-(3-hydroxybutanoyl)aminooctadecane-1,3-diol, (2S,3R)-2-{(S)-3-hydroxybutanoyl}aminooctadecane-1,3-diol, (2S,3R)-2-{(R)-3-hydroxybutanoyl)aminooctadecane-1,3-diol, (2S,3R)-2-(3-hydroxypentanoyl)aminooctadecane-1,3-diol, (2S,3R)-2-{(S)-3-hydroxypentanoyl}aminooctadecane-1,3-diol, (2S, 3R)-2-{(R)-3-hydroxypentanoyl)aminooctadecane-1,3-diol, (2S,3R)-2-(3-hydroxyhexanoyl)aminooctadecane-1,3-diol, (2S,3R)-2-{(S)-3-hydroxyhexanoyl}aminooctadecane-1,3-diol, (2S,3R)-2-{(R)-3-hydroxyhexanoyl)aminooctadecane-1,3-diol, (2S,3R)-2-(3-hydroxyoctanoyl)aminooctadecane-1,3-diol, (2S,3R)-2-{(S)-3-hydroxyoctanoyl}aminooctadecane-1,3-diol, (2S,3R)-2-{(S)-3-hydroxyoctanoyl}aminooctadecane-1,3-diol, (2S,3R)-2-{(R)-3-hydroxyoctanoyl}aminooctadecane-1,3-diol, (2S, 3R)-2-{(3-hydroxydecanoyl}aminooctadecane-1,3-diol, (2S,3R)-2-{(S)-3-hydroxydecanoyl}aminooctadecane-1,3-diol, (2S,3R)-2-{(R)-3-hydroxydecanoyl)aminooctadecane-1,3-diol, (2S,3R)-2-(3-hydroxydodecanoyl) aminooctadecane-1,3-diol, (2S,3R)-2-{(S)-3-hydroxydodecanoyl}aminooctadecane-1,3-diol, (2S,3R)-2-{(R)-3-hydroxydodecanoyl}aminooctadecane-1,3-diol, (2S, 3R)-2-2-(3-hydroxytetradecanoyl)aminooctadecane-1,3-diol, (2S,3R)-2-{(S)-3-hydroxytetradecanoyl}aminooctadecane-1,3-diol, (2S,3R)-2-{(R)-3-hydroxytetradecanoyl}aminooctadecane-1,3-diol, (2S,3R)-2-(3-hydroxyhexadecanoyl)aminooctadecane-1,3-diol, (2S,3R)-2-{(S)-3-hydroxyhexadecanoyl}aminooctadecane-1,3-diol, (2S,3R)-2-{(R)-3-hydroxyhexadecanoyl}aminooctadecane-1,3-diol, (2S,3R)-2-(3-hydroxyoctadecanoyl)aminooctadecane-1,3-diol, (2S,3R)-2-{(S)-3-hydroxyoctadecanoyl}aminooctadecane1,3-diol, (2S,3R)-2-{(R)-3-hydroxyoctadecanoyl)aminooctadecane-1,3-diol, (2S,3R)-2-(3-hydroxyicosanoyl)aminooctadecane-1,3-diol, (2S,3R)-2-{(S)-3-hydroxyicosanoyl}aminooctadecane-1,3-diol, (2S,3R)-2-{(R)-3-hydroxyicosanoyl} aminooctadecane-1,3-diol, (2S,3R)-2-(3-hydroxytetracosanoyl)aminooctadecane-1,3-diol, (2S,3R)-2-{(S)-3-hydroxytetracosanoyl}aminooctadecane-1,3-diol, and (2S,3R)-2-{(R)-3-hydroxytetracosanoyl} aminooctadecane-1,3-diol, and 4) (2S,3R)-2-oleoylaminooctadecane-1,3-diol, (2S,3R)-2-linoleylaminooctadecane-1,3-diol, (2S,3R)-2-linolenylaminoactadecane-1,3-diol and (2S,3R)-2-palmitoleylaminooctadecane-1,3-diol.

Although there is no particular limitation imposed on the process for preparing the compound of the formula (I), those exemplified in 1) to 4) can be employed depending on the kind of $R^2$.

1) When $R^2$ represents a saturated fatty acid group such as acetic acid, propionic acid, butanoic acid, pentanoic acid, hexanoic acid, octanoic acid, decanoic acid, dodecanoic acid, tetradecanoic acid, hexadecanoic acid, octadecanoic acid, icosanoic acid, docosanoic acid or tetracosanoic acid, the process as described in JP-A-4-327563 can be applied.

2) When $R^2$ represents a 2-hydroxy acid such as glycolic acid, lactic acid, (S)-lactic acid, (R)-lactic acid, 2-hydroxybutanoic acid, (S)-2-hydroxybutanoic acid, (R)-2-hydroxyheptanoic acid, 2-hydroxyhexanoic acid, (S)-2-hydroxyhexanoic acid, (R)-2-hydroxyhexanoic acid, 2-hydroxyoctanoic acid, (S)-2-hydroxyoctanoic acid, (R)-2-hydroxyoctanoic acid, 2-hydroxydecanoic acid, (S)-2-hydroxydecanoic acid, (R)-2-hydroxydecanoic acid, 2-hydroxydodecanoic acid, (S)-2-hydroxydodecanoic acid, (R)-2-hydroxydodecanoic acid, 2-hydroxytetradecanoic acid, (S)-2-hydroxytetradecanoic acid, (R)-2-hydroxytetradecanoic acid, 2-hydroxyhexadecanoic acid, (S)-2-hydroxyhexadecanoic acid, (R)-2-hydroxyhexadecanoic acid, 2-hydroxyoctadecanoic acid, (S)-2-hydroxyoctadecanoic acid, (R)-2-hydroxyoctadecanoic acid, 2-hydroxyicosanoic acid, (S)-2-hydroxyicosanoic acid, (R)-2-hydroxyicosanoic acid, 2-hydroxytetracosanoic acid, (S)-2-hydroxytetracosanoic acid or (R)-2-hydroxytetracosanoic acid, a process as described in JP-A-10-287350 can be applied.

3) When $R^2$ represents 3-hydroxypropionic acid, 3-hydroxybutanoic acid, (S)-3-hydroxybutanoic acid, (R)-3-hydroxybutanoic acid, 3-hydroxyhexanoic acid, (S)-3-hydroxyhexanoic acid, (R)-3-hydroxyhexanoic acid, 3-hydroxyoctanoic acid, (S)-3-hydroxyoctanoic acid, (R)-3-hydroxyoctanoic acid, 3-hydroxydecanoic acid, (S)-3-hydroxydecanoic acid, (R)-3-hydroxydecanoic acid, 3-hydroxydodecanoic acid, (S)-3-hydroxydodecanoic acid, (R)-3-hydroxydodecanoic acid, 3-hydroxytetradecanoic acid, (S)-3-hydroxytetradecanoic acid, (R)-3-hydroxytetradecanoic acid, 3-hydroxy hexadecanoic acid, (S)-3-hydroxyhexadecanoic acid, (R)-3-hydroxyhexadecanoic acid, 3-hydroxyoctadecanoic acid, (S)-3-hydroxystearic acid, (R)-3-hydroxyoctadecanoic acid or the like, the process as described in JP-A-10-218851 can be employed or applied.

5) When $R^2$ represents an unsaturated fatty acid group such as oleic acid, linoleic acid, linoleinic acid or palmitoleic acid, the process as described in JP-A-4-327563 can be employed or applied.

No particular limitation is imposed on the preparing process of the compound of the formula (I) and the present invention is not limited to the above-described preparation process.

The compounds of the formula (I) can be used either singly or in combination.

Each of the compounds of the formula (I) according to the present invention can be provided for practical use as a keratin fiber strengthening agent in admixture with at least one cosmetic raw material currently used in the art.

No particular limitation is imposed on the kind of the raw material in the present invention, and examples include oil components, lipids, sterols, lower or polyhydric alcohols, surfactants and other components;

Examples of the oil component include hydrocarbons such as paraffin, vaseline, ceresin, squalane, and squalene; higher fatty acids such as stearic acid, palmitic acid and isostearic acid; and higher alcohols such as palmityl alcohol, stearyl alcohol, cetanol, behenyl alcohol.

Examples of the lipid include glycerolipids such as eucalyptus oil, hardened palm oil, coconut oil, beeswax, tallow, lard and hydrous lanolin; sphingolipids such as ceramide, sphingomyelin, cerebroside and ganglioside; and lipid analogues such as racemic ceramide and pseudoceramide.

Examples of the sterol include cholesterol; ergosterol; phytosterols such as sitosterol, stigmasterol and spinasterol; and cholesterol esters such as cholesteryl isostearate, cholesteryl hydroxystearate and monocholesteryl succinate.

Examples of the lower alcohol or polyols include ethanol, glycerin, ethylene glycol, propylene glycol and 1,3-butyleneglycol.

Examples of the surfactant include higher fatty acid salts such as sodium stearate, sodium isostearate and sodium palmitate; anionic surfactants such as sodium stearoyl sulfate, sodium polyoxyethylene lauryl sulfate, sodium polyoxyethylene myristyl sulfate, sodium polyoxyethylene stearyl sulfate, sodium polyoxyethylene isostearyl sulfate, triethanolamine lauryl sulfate and hydroxymethyl cellulose sodium lauryl sulfate; cationic surfactants such as quaternary ammonium salts; and nonionic surfactants such as glyceryl monocaprate, glyceryl monocaprylate, glyceryl monooleate, glyceryl mono (2-ethylhexanoate), glyceryl monostearate, glycerin monopalmitate, cetyl monoglyceride octanoate, polyethylene glycol monostearate, hydroxyethyl cellulose, hydroxypropylmethyl cellulose, carboxyvinyl polymer, xanthan gum, glycerin monostearate esters and glycerin distearate esters.

Examples of the other components include antiseptics such as paraben, chelating agents such as sodium ethylenediaminetetraacetate, buffers such as citric acid, salts, perfumes and water.

The keratin fiber strengthening agent according to the present invention contains at least one compound of the formula (I) in a concentration of 0.001 to 20% by weight, preferably 0.005 to 5% by weight, more preferably 0.01 to 2% by weight, of total ceramide components based on the total composition.

As described later in Examples 31 to 38, the efficacy of keratin fiber strengthening agent of the present invention, containing a naturally occurring type of optically active substance, (2S,3R)-2-acylaminoalkane-1,3-diol represented by the formula (I), has been evaluated by use of healthy dog hair or healthy human hair which has been cut off and discarded in a beauty parlor. As a result, the hair damaged with degreasing treatment with an organic solvent (a chloroform/ethanol mixture) and then treated with the agent of the present invention has a significantly increased breaking strength and an improved Young's modulus as compared with the degreased hair by degreasing treatment, proving that the keratin fiber strengthening agent of the present invention is excellent in bringing about a significant improvement in the physical properties of keratin fiber, such as breaking strength.

Furthermore, it has been recognized that the hair treated with the keratin fiber strengthening agent of the present invention containing the compound of the formula (I) heightened the breaking strength significantly and improved Young's modulus as compared with the hair treated with a keratin fiber strengthening agent comprising a "racemic ceramide", which is a mixture of the stereoisomers of the compound represented by the formula (I) so that the agent of the present invention is effective in markedly improving the physical properties of keratin fiber such as breaking strength. These results apparently show that the keratin fiber strengthening agent according to the present invention exhibits effects to keratin fibers for increasing the breaking strength, and high toughness. The organic solvent used here is a mixture of chloroform and ethanol, by which a lipid component can be extracted easily. The mixing ratio of chloroform and ethanol is from 1:1 to 10:1. The term "degreasing treatment with an organic solvent" as used herein means the treatment for removing lipid components from the hair by immersing healthy hair in the organic solvent and subjecting it to ultrasonication for 15 minutes.

A hair cosmetic composition such as shampoo, rinse or hair protecting cream can be formulated by incorporating cosmetic raw materials in the compound of the formula (I) of the present invention and adding an antiseptic such as methyl paraben or ethyl paraben.

The paraben described in the below-described Examples is a 1:1 mixture of methyl paraben and ethyl paraben. By treating the hair, which has been damaged by permanent wave, bleaching, exposure to ultraviolet light or the like, with a hair care cosmetic such as shampoo, rinse, hair protecting cream or lotion formulated by using the compound of the formula (I) in accordance with the formulation as described later in Examples, it is possible to improve the breaking strength of keratin, that is, to improve the strength of keratin fiber. Similarly, the breaking strength of the dog hair can be improved by cosmetics such as shampoo, hair-protecting cream, lotion or the like for dogs which are formulated in accordance with the method as described later in Examples.

The present invention will now be illustrated in detail with respect to Examples, but it should be understood that the present invention is not construed as being limited thereto. Unless otherwise noted, all the percents and ratios are by weight.

EXAMPLE 1

Preparation of Keratin Fiber Strengthening Agent

| | |
|---|---|
| Compound 1 | 0.8% |
| Isostearic acid | 0.3% |
| Sodium stearate | 0.3% |
| Cholesterol | 0.3% |
| Glycerol monostearate | 0.1% |
| Cetanol | 0.1% |
| Sodium polyoxyethylene lauryl ether sulfate | 10.0% |
| Propylene glycol | 10.0% |
| Purified water | balance |

Isostearic acid, sodium stearate, cholesterol, glycerol monostearate, and cetanol were added to, (2S,3R)-2-octadecanoylaminooctadecane-1,3-diol(compound 1), and the mixture was heated at 100 to 120° C. to prepare a solution. Propylene glycol was added to the solution at about 70° C., followed by stirring to make the mixture uniform. Polyoxyethylene lauryl ether sodium sulfate was added thereto, and purified water was further added at about 70° C. while stirring to prepare a keratin fiber strengthening agent.

COMPARATIVE EXAMPLE 1

Preparation of Blank Treating agent

The same components as used in Example 1 except compound 1 were compounded in the same manner as in Example 1 to obtain a blank treating agent.

COMPARATIVE EXAMPLE 2

Preparation of Treating Agent Containing Racemate

A comparative treating agent was prepared in the same manner as in Example 1, except for replacing compound 1 with a racemic ceramide having the same planar structure as compound 1.

EXAMPLE 2

A keratin fiber strengthening agent was obtained in the same manner as in Example 1, except for replacing compound 1 with, (2S,3R)-2-hexadecanoylaminohexadecane-1,3-diol (compound 2).

EXAMPLE 3

A keratin fiber strengthening agent was obtained in the same manner as in Example 1, except for replacing compound 1 with a 1:1 mixture of compound 1 and, (2S,3R)-2-octadecanoylaminoicosadecane-1,3-diol (compound 3).

EXAMPLE 4

A keratin fiber strengthening agent was obtained in the same manner as in Example 1, except for replacing compound 1 with, (2S,3R)-2-octadecanoylaminohexadecane-1,3-diol (compound 4).

EXAMPLE 5

A keratin fiber strengthening agent was obtained in the same manner as in Example 1, except for replacing compound 1 with a 1:2 mixture of compound 2 and compound 4.

EXAMPLE 6

A keratin fiber strengthening agent was obtained in the same manner as in Example 1, except for replacing compound 1 with a 3:1 mixture of compound 2 and compound 3.

EXAMPLE 7

A keratin fiber strengthening agent was obtained in the same manner as in Example 1, except for replacing compound 1 with a 1:1:1 mixture of compound 2, compound 3, and compound 1.

EXAMPLE 8

Preparation of Hair Cream

Hair cream was prepared from the following components.

| | |
|---|---|
| Compound 1 | 0.6% |
| Liquid paraffin | 15.0% |
| Vaseline | 15.0% |
| Beezwax | 2.0% |
| Carboxyvinyl polymer | 0.1% |
| Xantham gum | 0.1% |

-continued

| | |
|---|---|
| Glycerol | 5.0% |
| Polyoxyethylene hydrogenated castor oil | 3.0% |
| Chelating agent | adequate amount |
| Isostearic acid | 0.3% |
| Sodium stearate | 0.3% |
| Cholesterol | 0.3% |
| Cetanol | 0.1% |
| Paraben* | adequate amount |
| Perfume | adequate amount |
| Purified water | balance |

*1:1 mixture of methyl p-hydroxybenzoate and butyl p-hydroxybenzoate

EXAMPLE 9

Preparation of Hair Cream

Hair cream was prepared from the following components.

| | |
|---|---|
| 1:1 Mixture of compound 3 and compound 1 | 0.6% |
| Liquid paraffin | 15.0% |
| Vaseline | 15.0% |
| Beezwax | 2.0% |
| Carboxyvinyl polymer | 0.1% |
| Xantham gum | 0.1% |
| Glycerol | 5.0% |
| Polyoxyethylene hydrogenated castor oil | 3.0% |
| Chelating agent | adequate amount |
| Isostearic acid | 0.3% |
| Sodium stearate | 0.3% |
| Cholesterol | 0.3% |
| Paraben | adequate amount |
| Cetanol | 0.1% |
| Perfume | adequate amount |
| Purified water | balance |

EXAMPLE 10

Preparation of Shampoo

A shampoo was prepared from the following components.

| | |
|---|---|
| Compound 1 | 1.0% |
| Triethanolamine laurylsulfate | 18.5% |
| 1% Aqueous solution of hydroxypropyl-methyl cellulose | 15.0% |
| Ammonium laurylsulfate | 8.0% |
| 1,3-Dimethylol-5,5-dimethylhydantoin | 0.15% |
| Disodium ethylenediaminetetraacetate | 0.05% |
| Citric acid | small amount |
| Sodium chloride | small amount |
| Perfume | 0.85% |
| Isostearic acid | 0.3% |
| Sodium stearate | 0.3% |
| Cholesterol | 0.3% |
| Glycerol monostearate | 0.1% |
| Cetanol | 0.1% |
| Purified water | balance |

EXAMPLE 11

Preparation of Shampoo

A shampoo was prepared from the following components.

| | |
|---|---|
| 1:1 Mixture of compound 3 and compound 1 | 1.0% |
| Triethanolamine laurylsulfate | 18.5% |
| 1% Aqueous solution of hydroxypropyl-methyl cellulose | 15.0% |
| Ammonium laurylsulfate | 8.0% |
| 1,3-Dimethylol-5,5-dimethylhydantoin | 0.15% |
| Disodium ethylenediaminetetraacetate | 0.05% |
| Citric acid | small amount |
| Sodium chloride | small amount |
| Perfume | 0.85% |
| Isostearic acid | 0.3% |
| Sodium stearate | 0.3% |
| Cholesterol | 0.3% |
| Glycerol monostearate | 0.1% |
| Cetanol | 0.1% |
| Purified water | balance |

EXAMPLE 12

Preparation of Shampoo

A shampoo was prepared from the following components.

| | |
|---|---|
| 1:1:1 Mixture of compound 2, compound 3 and compound 1 | 0.9% |
| Triethanolamine laurylsulfate | 18.5% |
| 1% Aqueous solution of hydroxypropyl-methyl cellulose | 15.0% |
| Ammonium laurylsulfate | 8.0% |
| 1,3-Dimethylol-5,5-dimethylhydantoin | 0.15% |
| Disodium ethylenediaminetetraacetate | 0.05% |
| Citric acid | small amount |
| Sodium chloride | small amount |
| Perfume | 0.85% |
| Isostearic acid | 0.3% |
| Sodium stearate | 0.3% |
| Cholesterol | 0.3% |
| Glycerol monostearate | 0.1% |
| Cetanol | 0.1% |
| Purified water | balance |

EXAMPLE 13

Preparation of Dog Shampoo

A dog shampoo was prepared from the following components.

| | |
|---|---|
| 1:1:1 Mixture of compound 2, compound 3 and compound 1 | 0.6% |
| Triethanolamine laurylsulfate | 18.5% |
| 1% Aqueous solution of hydroxypropyl-methyl cellulose | 15.0% |
| Ammonium laurylsulfate | 8.0% |
| 1,3-Dimethylol-5,5-dimethylhydantoin | 0.15% |
| Disodium ethylenediaminetetraacetate | 0.05% |
| Citric acid | small amount |
| Sodium chloride | small amount |
| Perfume | 0.85% |
| Isostearic acid | 0.3% |
| Sodium stearate | 0.3% |
| Cholesterol | 0.3% |
| Glycerol monostearate | 0.1% |

| | |
|---|---|
| Cetanol | 0.1% |
| Purified water | balance |

EXAMPLE 14

Preparation of Dog Shampoo

A dog shampoo was prepared from the following components.

| | |
|---|---|
| Compound 2 | 0.6% |
| Triethanolamine laurylsulfate | 18.5% |
| 1% Aqueous solution of hydroxypropyl-methyl cellulose | 15.0% |
| Ammonium laurylsulfate | 8.0% |
| 1,3-Dimethylol-5,5-dimethylhydantoin | 0.15% |
| Disodium ethylenediaminetetraacetate | 0.05% |
| Citric acid | small amount |
| Sodium chloride | small amount |
| Perfume | 0.85% |
| Isostearic acid | 0.3% |
| Sodium stearate | 0.3% |
| Cholesterol | 0.3% |
| Glycerol monostearate | 0.1% |
| Cetanol | 0.1% |
| Purified water | balance |

EXAMPLE 15

Preparation of Hair Lotion

Hair lotion was prepared from the following components.

| | |
|---|---|
| 1:1:1 Mixture of compound 2, compound 3 and compound 1 | 1.0% |
| Hydroxyethyl cellulose | 0.4% |
| Ethanol | 25.0% |
| Glycerol monooleate | 2.0% |
| Paraben | 0.2% |
| Perfume | 0.1% |
| Isostearic acid | 0.3% |
| Sodium stearate | 0.3% |
| Cholesterol | 0.3% |
| Glycerol monostearate | 0.1% |
| Cetanol | 0.1% |
| Purified water | balance |

EXAMPLE 16

Preparation of Dog Hair Lotion

Dog hair lotion was prepared from the following components.

| | |
|---|---|
| Compound 1 | 0.5% |
| Hydroxyethyl cellulose | 0.4% |
| Ethanol | 25.0% |
| Glycerol monooleate | 2.0% |
| Paraben | 0.2% |
| Perfume | 0.1% |
| Isostearic acid | 0.3% |
| Sodium stearate | 0.3% |
| Cholesterol | 0.3% |
| Glycerol monostearate | 0.1% |
| Cetanol | 0.1% |
| Purified water | balance |

EXAMPLE 17

Preparation of Hair Lotion

Hair lotion was prepared from the following components.

| | |
|---|---|
| 1:1 Mixture of compound 3 and compound 1 | 1.0% |
| Hydroxyethyl cellulose | 0.4% |
| Ethanol | 25.0% |
| Glycerol monooleate | 2.0% |
| Paraben | 0.2% |
| Perfume | 0.1% |
| Isostearic acid | 0.3% |
| Sodium stearate | 0.3% |
| Cholesterol | 0.3% |
| Glycerol monostearate | 0.1% |
| Cetanol | 0.1% |
| Purified water | balance |

EXAMPLE 18

Dog hair lotion was prepared from the following components.

| | |
|---|---|
| 1:1:1 Mixture of compound 2, compound 3 and compound 1 | 0.9% |
| Hydroxyethyl cellulose | 0.4% |
| Ethanol | 25.0% |
| Glycerol monooleate | 2.0% |
| Paraben | 0.2% |
| Perfume | 0.1% |
| Isostearic acid | 0.3% |
| Sodium stearate | 0.3% |
| Cholesterol | 0.3% |
| Glycerol monostearate | 0.1% |
| Cetanol | 0.1% |
| Purified water | balance |

EXAMPLE 19

Hair lotion was prepared from the following components.

| | |
|---|---|
| 1:1:1 Mixture of compound 2, compound 3 and compound 1 | 1.0% |
| Hydroxyethyl cellulose | 0.4% |
| Ethanol | 25.0% |
| Glycerol monooleate | 2.0% |
| Paraben | 0.2% |
| Perfume | 0.1% |
| Isostearic acid | 0.3% |
| Sodium stearate | 0.3% |
| Cholesterol | 0.3% |
| Glycerol monostearate | 0.1% |
| Cetanol | 0.1% |
| Purified water | balance |

EXAMPLE 20

Preparation of Dog Hair Lotion

Dog hair lotion was prepared from the following components.

| | |
|---|---|
| 2:1 Mixture of compound 3 and compound 1 | 0.9% |
| Hydroxyethyl cellulose | 0.4% |
| Ethanol | 25.0% |
| Glycerol monooleate | 2.0% |
| Paraben | 0.2% |
| Perfume | 0.1% |
| Purified water | balance |

EXAMPLE 21

Preparation of Keratin Fiber Strengthening Agent

A keratin fiber strengthening agent was prepared in the same manner to Example 1 except for replacing compound 1 with compound 6, (2S,3R)-2-(2-hydroxyhexadecanoyl) aminooctadecane-1,3-diol.

| Component | wt. % |
|---|---|
| Compound 6 | 0.8 |
| Isostearic acid | 0.3 |
| Sodium stearate | 0.3 |
| Cholesterol | 0.3 |
| Glycerol monostearate | 0.1 |
| Cetanol | 0.1 |
| Sodium polyoxyethylene lauryl ether sulfate | 10.0 |
| Propylene glycol | 10.0 |
| Purified water | balance |

COMPARATIVE EXAMPLE 3

Preparation of Blank Treating Agent

In a similar manner to Example 1 except that Compound 1 was eliminated from the formulation of Example 1, a treating agent (placebo treating agent) was prepared.

EXAMPLE 22

Formulation Example of Keratin Fiber Strengthening Agent

In a similar manner to Example 21 except that as the ceramide of the formula (I), (2S,3R)-2-oleoylaminooctadecane-1,3-diol (Compound 7) containing as $R^1$ a $C_{15}H_{31}$ group and as $R^2$ an oleoyl group was used instead of Compound 6, a keratin fiber strengthening agent (an optical-active-substance-containing treating agent of the present invention) was prepared.

EXAMPLE 23

Formulation Example of Keratin Fiber Strengthening Agent

In a similar manner to Example 21 except that as a ceramide of the formula (I), a 2:1 mixture of (2S,3R)-2-octadecanoylaminooctadecane-1,3-diol (Compound 1) containing as $R^1$ a $C_{15}H_{31}$ group and as $R^2$ an octadecanoyl group and ((2S,3R)-2-acetylamino)octadecane-1,3-diol (Compound 8) containing as $R^1$ a $C_{15}H_{31}$ group and as $R^2$ an acetyl group was used instead of single use of Compound 6, a keratin fiber strengthening agent was prepared.

EXAMPLE 24

Formulation Example of Keratin Fiber Strengthening Agent

In a similar manner to Example 21 except that as a ceramide of the formula (I), (2S,3R)-2-{(R)-3-hydroxyhexadecanoyl)amino}octadecane-1,3-diol (Compound 9) containing as $R^1$ a $C_{15}H_{31}$ group and as $R^2$ an (R)-3-hydroxyhexadecanoyl group was used instead of Compound 6, a keratin fiber strengthening agent was prepared.

EXAMPLE 25

Formulation Example of Keratin Fiber Strengthening Agent

In a similar manner to Example 21 except that as a ceramide of the formula (I), (2S,3R)-2-{(R)-2-hydroxyhexadecanoyl)amino}octadecane-1,3-diol (Compound 10) containing as $R^1$ a $C_{15}H_{31}$ group and as $R^2$ an (R)-2-hydroxyhexadecanoyl group was used instead of Compound 6, a keratin fiber strengthening agent was prepared.

EXAMPLE 26

Preparation of Hair Treating Agent

A hair treating agent was prepared using as a ceramide of the formula (I), (2S,3R)-2-(2-hydroxyhexadecanoyl) aminooctadecane-1,3-diol (Compound 6) containing as $R^1$ a $C_{15}H_{31}$ group and as $R^2$ a 2-hydroxyhexadecanoyl group.

| Component | wt. % |
|---|---|
| Compound 6 | 0.6 |
| Liquid paraffin | 15.0 |
| Vaseline | 15.0 |
| Beeswax | 2.0 |
| Carboxyvinyl polymer | 0.1 |
| Xanthan gum | 0.1 |
| Glycerin | 5.0 |
| Polyoxyethylene hydrogenated castor oil | 3.0 |
| Chelating agent | adequate amount |
| Isostearic acid | 0.3 |
| Sodium stearate | 0.3 |
| Cholesterol | 0.3 |
| Cetanol | 0.1 |
| Paraben | adequate amount |
| Perfume | adequate amount |
| Purified water | balance |

EXAMPLE 27

Preparation of Hair Treating Agent

A hair treating agent was prepared using, as a ceramide of the formula (I), (2S,3R)-2-oleoylaminooctadecane-1,3-diol (Compound 7) containing as $R^1$ a $C_{15}H_{31}$ group and as $R^2$ an oleoyl group.

| Component | wt. % |
|---|---|
| Compound 7 | 1.0 |
| Triethanolamine lauryl sulfate | 18.5 |
| A 1% aqueous solution of hydroxypropylmethyl cellulose | 15.0 |
| Ammonium lauryl sulfate | 8.0 |
| 1,3-dimethylol-5,5-dimethylhidantoin | 0.15 |
| Disodium ethylenediaminetetraacetate | 0.05 |
| Citric acid | small amount |
| Sodium chloride | small amount |
| Perfume | 0.85 |
| Isostearic acid | 0.3 |

EXAMPLE 28

Preparation of Hair Treating Agent

A hair treating agent was prepared using as a ceramide of the formula (I), a 7:1 mixture of (2S,3R)-2-octadecanoylaminooctadecane-1,3-diol (Compound 1) containing as $R^1$ a $C_{15}H_{31}$ group and as $R^2$ a 2-octadecanoyl group and (2S,3R)-2-(2-hydroxyhexadecanoyl)aminooctadecane-1,3-diol (Compound 6) containing as $R^1$ a $C_{15}H_{31}$ group and as $R^2$ a 2-hydroxyhexadecanoyl group.

| Component | wt. % |
| --- | --- |
| A 7:1 mixture of Compound 1 and Compound 6 | 3.0 |
| Triethanolamine lauryl sulfate | 18.5 |
| A 1% aqueous solution of hydroxypropylmethyl cellulose | 15.0 |
| Ammonium lauryl sulfate | 8.0 |
| 1,3-dimethylol-5,5-dimethylhydantoin | 0.15 |
| Disodium ethylenediaminetetraacetate | 0.05 |
| Citric acid | small amount |
| Sodium chloride | small amount |
| Perfume | 0.85 |
| Isostearic acid | 0.3 |
| Sodium stearate | 0.3 |
| Cholesterol | 0.3 |
| Glyceryl monostearate | 0.1 |
| Cetanol | 0.1 |
| Purified water | balance |

EXAMPLE 29

Preparation of Hair Treating Agent

A hair treating agent was prepared using as a ceramide of the formula (I), (2S,3R)-2-{(R)-3-hydroxyhexadecanoyl)amino}octadecane-1,3-diol (Compound 9) containing as $R^1$ a $C_{15}H_{31}$ group and as $R^2$ an (R)-3-hydroxyhexadecanoyl group.

| Component | wt. % |
| --- | --- |
| Compound 9 | 0.01 |
| Hydroxyethyl cellulose | 0.4 |
| Ethanol | 25.0 |
| Glyceryl monooleate | 2.0 |
| Paraben | 0.2 |
| Perfume | 0.1 |
| Isostearic acid | 0.3 |
| Sodium stearate | 0.3 |
| Cholesterol | 0.3 |
| Glyceryl monostearate | 0.1 |
| Cetanol | 0.1 |
| Purified water | balance |

EXAMPLE 30

Preparation of Hair Treating Agent

A hair treating agent was prepared using as a ceramide of the formula (I), (2S,3R)-2-{(R)-2-hydroxyhexadecanoyl)amino}octadecane-1,3-diol (Compound 10) containing as $R^1$ a $C_{15}H_{31}$ group and as $R^2$ an (R)-2-hydroxyhexadecanoyl group.

| Component | wt. % |
| --- | --- |
| Compound 10 | 0.5 |
| Hydroxyethyl cellulose | 0.4 |
| Ethanol | 25.0 |
| Glyceryl monooleate | 2.0 |
| Paraben | 0.2 |
| Perfume | 0.1 |
| Isostearic acid | 0.3 |
| Sodium stearate | 0.3 |
| Cholesterol | 0.3 |
| Glyceryl monostearate | 0.1 |
| Cetanol | 0.1 |
| Purified water | balance |

EXAMPLE 31

Breaking Strength Test

Hair samples 1 to 5 were prepared and subjected to a destructive test under the following conditions by the use of Shimadzu Autograph AGS-500B (manufactured by Shimadzu Corp.) to measure a breaking strength. The results obtained are shown in Table 1 below.

Measuring Conditions:
  Hair: A hair having a length of about 15 cm and a diameter of about 0.08 to 0.1 mm, clamped 5.7 cm from each end.
  Pulling speed: 5.0 cm/min
  Atmosphere: 25° C., 40% RH Preparation of Samples:
  Healthy hair, cut off from a 20-year-old female at a beauty parlor, which had not been permed nor bleached, was used.

The healthy hair (untreated hair, sample 1) weighing 50 g was soaked in 450 ml of a 2:1 (by volume) mixture of chloroform and ethanol and subjected to ultrasonication for 15 minutes to remove lipids. The sample was washed with 250 ml of a 2:1 (by volume) mixture of chloroform and ethanol and then with 100 ml of acetone and dried to prepare solvent-treated hair as damaged hair (sample 2).

The solvent-treated hair weighing 40 g was soaked in a 5-fold weight of each of the blank treating agent of Comparative Example 1, the racemate-containing treating agent of Comparative Example 2, and the keratin fiber strengthening agent of Example 1 and subjected to ultrasonication for 15 minutes, followed by washing with five 1000 ml portions of water. The treated hair was dried under reduced pressure at 60° C. 2 hours and then under reduced pressure for 3 hours to prepare samples 3 to 5, respectively.

TABLE 1

| Sample No. | Condition | Treatment | Breaking Strength* (kgf) |
| --- | --- | --- | --- |
| 1 | healthy | none | 0.1514 |
| 2 | damaged | none | 0.1278 |
| 3 | " | blank | 0.1682 |
| 4 | " | racemate | 0.1555 |
| 5 | " | compound 1 | 0.2058 |

Note: *Average of 10 measurements (n = 10), hereinafter the same.

Figure 1:
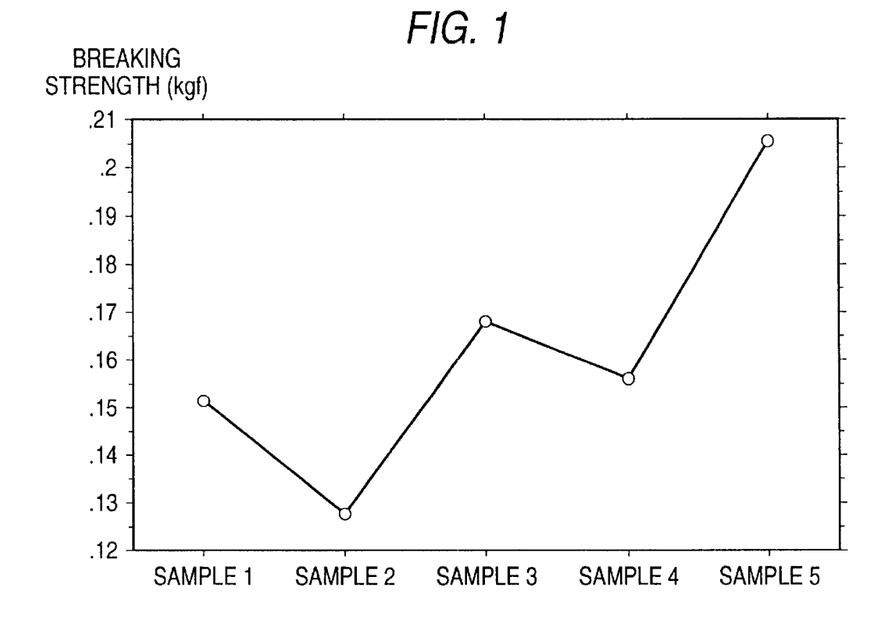
FIG. 1 is a graph of breaking strength of hair sampled from a 20-year-old female.

The results in Table 1 are graphically represented in FIG. 1. As is apparent from the results in Table 1 and FIG. 1, the keratin fiber strengthening agent of the present invention significantly increases the breaking strength of compared with the blank treating agent (P<0.01) or containing treating agent.

EXAMPLE 32

A keratin fiber strengthening agent containing a 1:1 mixture of compound 1 and compound 2, a 1:1 mixture of compound 1 and compound 3, or a 1:1 mixture of compound 2 and compound 3 in place of compound 1 was tested in the same manner as in Example 31. The results obtained were similar to those in Example 31.

EXAMPLE 33

Measurement of Young's Modulus

Healthy hair, cut off from a 25-year-old female at a beauty parlor, which had not been permed nor bleached, was used.

Healthy hair (untreated hair, sample 6) was treated with a chloroform-ethanol mixed solvent in the same manner as in Example 31 to prepare sample 7. Samples 8 to 10 were prepared in the same manner as for samples 3 to 5 of Example 31. The breaking strength of each sample was measured by means of Shimadzu Autograph. A Young's modulus was also measured. The results obtained are shown in Table 2 below.

TABLE 2

| Sample No. | Condition | Treatment | Young's Modulus* (kgf/mm) |
|---|---|---|---|
| 6 | healthy | none | 289.395 |
| 7 | damaged | none | 248.739 |
| 8 | " | blank | 271.162 |
| 9 | " | racemate | 300.163 |
| 10 | " | compound 1 | 338.360 |

Note: *Average of 10 measurements (n = 10), hereinafter the same.

Figure 2:
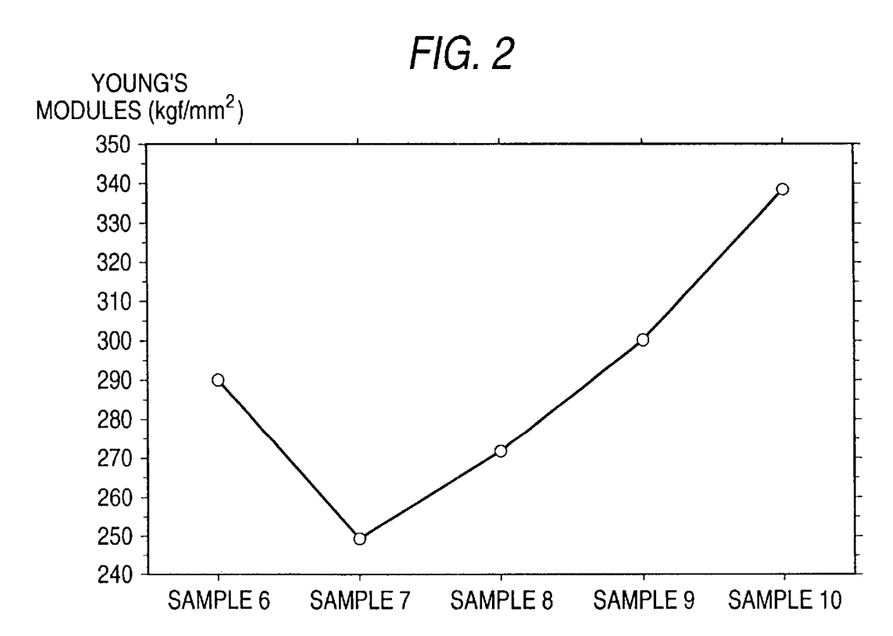
FIG. 2 is a graph of Young's modulus of hair sampled from a 25-year-old female.

The Young's modulus of samples 6 to 10 are graphically represented in FIG. 2. As shown in Table 2 and FIG. 2, the keratin fiber strengthening agent of the present invention significantly increases the Young's modulus of hair as compared with the blank treating agent (P<0.001) or racemate-containing treating agent.

EXAMPLE 34

A keratin fiber strengthening agent containing a 1:1 mixture of compound 1 and compound 2, a 1:1 mixture of compound 1 and compound 3, or a 1:1 mixture of compound 1 and compound 5 in place of compound 1 was tested in the same manner in Example 33. The results obtained were similar to those in Example 33.

EXAMPLE 35

Measurement of Toughness

The breaking strength and elongation measured on samples 6 to 10 in Example 33 are shown in Table 3 below. A toughness (a product of breaking strength and elongation) as calculated from these data (n=10) are also shown in Table 3.

TABLE 3

| Sample No. | Breaking Strength (kgf) | Elongation (mm) | Toughness (kgf × mm) |
|---|---|---|---|
| 6 | 0.2332 | 24.68 | 5.7554 |
| 7 | 0.2070 | 23.66 | 4.8976 |
| 8 | 0.2553 | 25.65 | 6.5484 |
| 9 | 0.2381 | 23.81 | 5.6692 |
| 10 | 0.2941 | 27.08 | 7.9642 |

Figure 3:
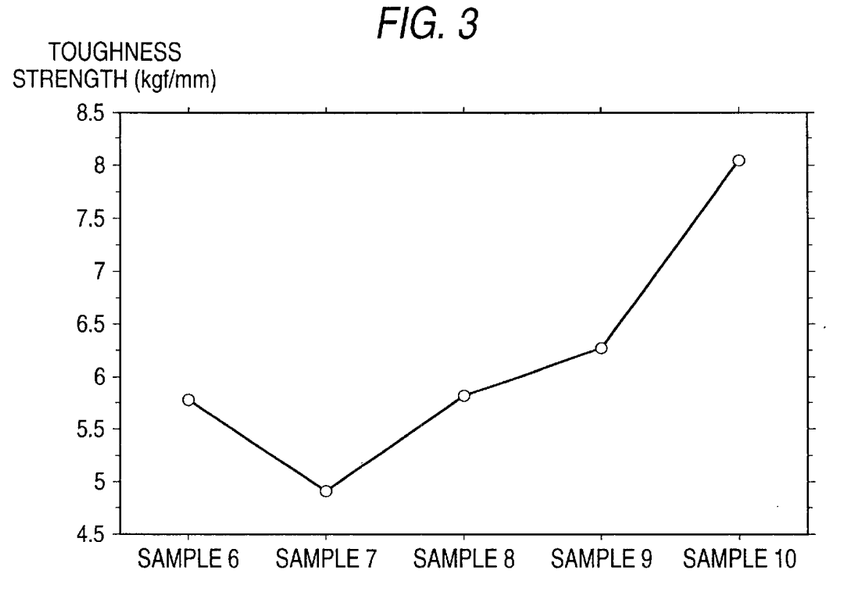
FIG. 3 is a graph of toughness of hair sampled from a 25-year-old female.

The data of toughness are graphically represented in FIG. 3. The results of Table 3 and FIG. 3 prove that the hair treated with the keratin fiber strengthening agent of the present invention gains increased toughness significantly over the hair samples treated with the blank (P<0.05) or the racemate-containing treating agent.

EXAMPLE 36

Breaking Strength Test on Dog Hair

Dog hair samples 11 to 15 were prepared as follows and subjected to a destructive test under the following conditions by the use of Shimadzu Autograph AGS-SOOB (manufactured by Shimadzu Corp.) to measure a breaking strength and a Young's modulus. The results obtained are shown in Table 4 below. The breaking strength and Young's modulus data obtained are also graphically represented in FIGS. 4 and 5, respectively.

Measuring Conditions:

Dog Hair: A dog hair having a length of about 10 to 15 cm and a diameter of about 0.08 to 0.1 mm, clamped 2 cm from each end.

Pulling speed: 5.0 cm/min

Atmosphere: 25° C., 40% RH

Preparation of Samples:

Healthy dog hairs collected from around the neck of a 4-year-old male Shetland sheepdog were used. The untreated hair as collected (sample 11) weighing 50 g was treated in the same manner as in Example 31 to prepare samples 12 to 15.

TABLE 4

| Sample No. | Condition | Treatment | Breaking Strength (kgf) (n = 10) | Breaking Strength per area (kgf/mm$^2$) | Young's Modulus (kgf/mm$^2$) (n = 10) |
|---|---|---|---|---|---|
| 11 | healthy | None | 0.1114 | 39.33 | 559.224 |
| 12 | damaged | None | 0.1032 | 37.09 | 535.528 |
| 13 | " | Blank | 0.1162 | 39.98 | 555.086 |
| 14 | " | Racemate | 0.1165 | 41.52 | 562.846 |
| 15 | " | compound 1 | 0.1196 | 42.55 | 605.240 |

Figure 4:
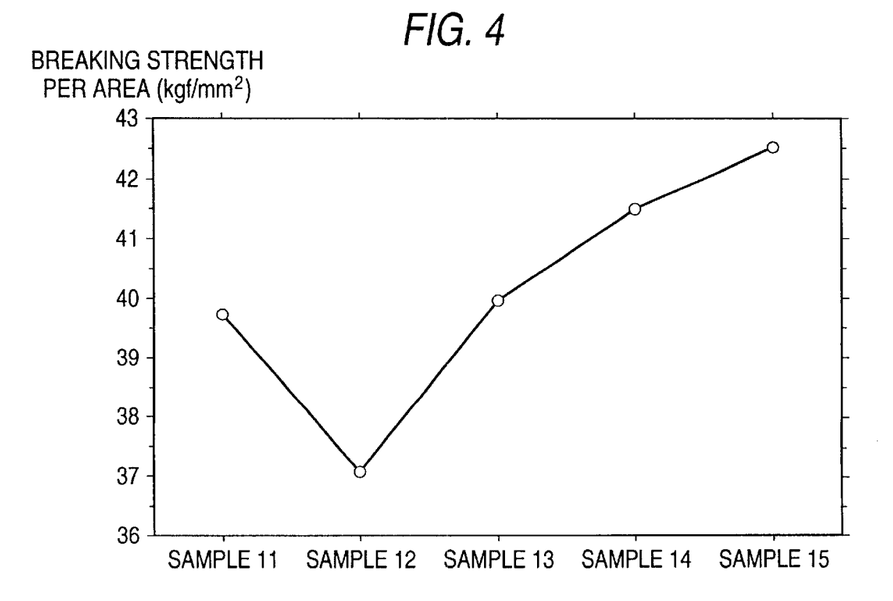
FIG. 4 is a graph of breaking strength of hair sampled from a 4-year-old male dog.
Figure 5:
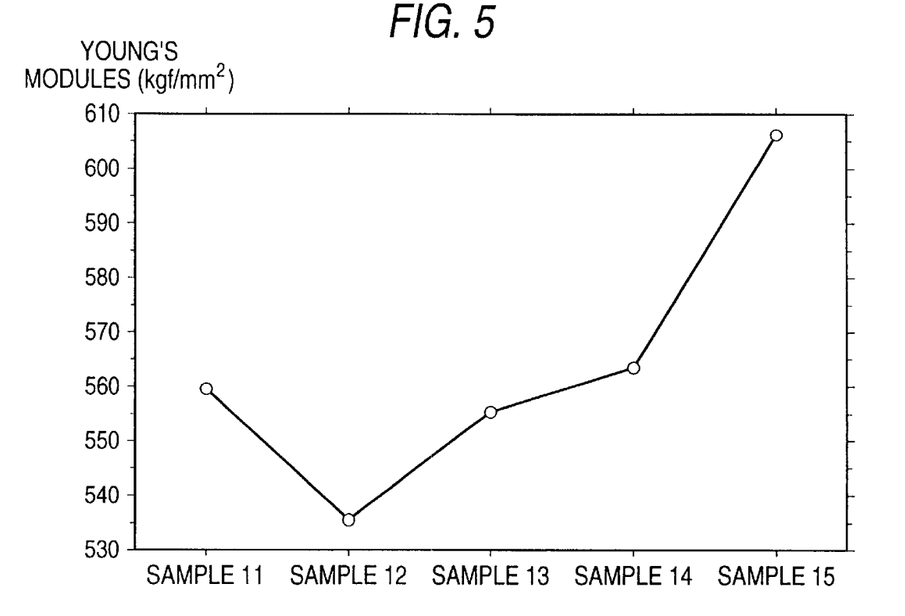
FIG. 5 is a graph of Young's modulus of hair sampled from a 4-year-old male dog.

As is apparent from the results in Table 4 and FIGS. 4 and 5, the keratin fiber strengthening agent of the present invention significantly increases the breaking strength (P<0.05) and the Young's modulus (P<0.005) as compared with the blank treating agent or racemate-containing treating agent.

It has been thus proved that the keratin fiber strengthening agent containing compound 1 brings about significant improvements on breaking strength and Young's modulus for not only human hair but dog hair.

EXAMPLE 37

A keratin fiber strengthening agent containing compound 5 or a 1:1 mixture of compound 1 and compound 2 in place of compound 1 was tested in the same manner as in Example 36. The results obtained were similar to those in Example 36.

EXAMPLE 38

Breaking strength test

Samples (Samples 16 to 19) were prepared as described below and breaking strength test and measurement of elongation were carried out under the below-described measuring conditions by using Shimadzu Autograph AGS0599B (manufactured by Simadzu Corp). Based on the results, toughness (breaking strength×elongation) of each of Samples 16 to 19 was calculated.

(a) Testing method

Relative humidity: 40%, temperature: 25° C.

Hair employed for the test: A hair having a length of about 15 cm and a diameter of about 0.08 to 0.1 mm, clamped 5.0 cm from each end.

Pulling speed: 5.0 cm/min (b) Preparation of Samples (Samples 16 to 19)

Healthy hair, cut off from a 18-year-old female at a beauty parlor, which had not been permed nor bleached, was used.

The healthy hair (untreated hair, Sample 16) weighing 50 g was soaked in 450 ml of a 2:1 mixture of chloroform and ethanol and subjected to ultrasonication for 15 minutes to remove lipid components. The sample was then washed with 250 ml of a 2:1 mixture of chloroform and ethanol and then with 100 ml of acetone, followed by drying under reduced pressure, whereby organic-solvent-treated hair (Sample 17) was obtained.

The solvent-treated hair (Sample 17) weighing 40 g was soaked in a 5-fold weight of each of the treating agents and subjected to ultrasonication for 15 minutes. The hair was then washed five times with 1000 ml of water, followed by drying at 60° C. for 2 hours under reduced pressure and then drying for 3 hours under reduced pressure, whereby each of Samples 18 to 19 were obtained. Described specifically, Sample 18 was the hair treated with the treating agent (placebo treating agent), which had been prepared in Comparative Example 3, subsequent to the treatment with a solvent, while Sample 19 was the hair treated with the keratin fiber strengthening agent of the present invention (Compound-6-containing treating agent) which had been prepared in Example 21.

The differences of the samples are summarized as follows.

Sample 16: Healthy hair (untreated)

Sample 17: Hair treated with the solvent

Sample 18: Hair treated with the solvent and then with the placebo treating agent prepared in Comparative Example Sample 19: Hair treated with the solvent and then with the keratin fiber strengthening agent of the present invention (Compound-6-containing treating agent) prepared in Example 31

(C) Results

The mean value (n=10) of each of the breaking strength (Kgf), elongation (mm) and toughness (Kgf/m) was as follows:

|  | Breaking strength (Kgf) | Elongation (mm) | Toughness (Kg/mm) |
|---|---|---|---|
| Sample 16 | 0.246 | 27.16 | 6.681 |
| Sample 17 | 0.191 | 24.97 | 4.769 |
| Sample 18 | 0.201 | 23.01 | 4.625 |
| Sample 19 | 0.266 | 26.02 | 6.921 |

Figure 6:
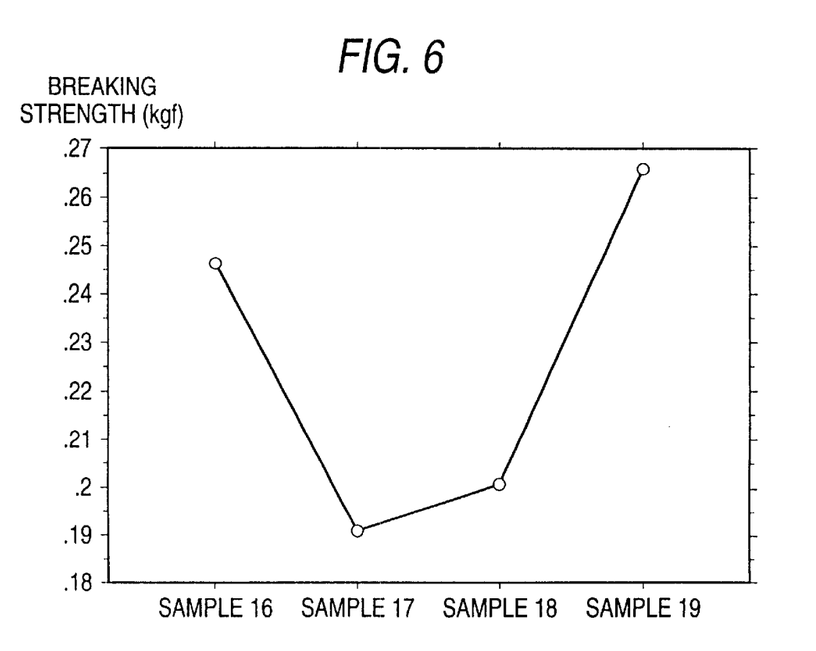
FIG. 6 is a graph of breaking strength of hair sampled from a 18-year-old female.

As is obvious from the results in the above Table or FIG. 6, the keratin fiber strengthening agent of the present invention containing Compound 6 (Sample 19) significantly increases the breaking strength of hair (P<0.05) as compared with the placebo treating agent (Sample 18).

It has been confirmed that the keratin fiber strengthening agent comprising an optically active (2S,3R)-2-acylaminoalkane-1,3-diol represented by the formula (I), which has the same steric configuration as naturally occurring ceramide, is effective for markedly increasing the breaking strength of hair when applied to keratin fiber such as hair by adhesion, coating or impregnation. It has been ascertained that the keratin fiber strengthening agent according to the present invention brings about a marked improvement in breaking strength and Young's modulus of hair as compared with a keratin fiber strengthening agent comprising a "racemic ceramide" which is a mixture of stereoisomers of the above-described compound. From these results, it is understood that hair care products for restoring the damaged hair can be developed by using the keratin fiber strengthening agent of the present invention. It is also been understood that the keratin fiber strengthening agent of the present invention has a curative effect in restoring damaged hair.

While the invention has been described in detail and with reference to specific embodiments thereof, it will be apparent to one skilled in the art that various changes and modifications can be made therein without departing from the spirit and scope thereof.

What is claimed is:

1. A method for improving the strength of keratin fiber, which comprises applying a keratin fiber strengthening agent comprising:

0.001 to 20% by weight of at least one (2S,3R)-2-acylaminoalkane-1,3-diol represented by the following formula (I):

wherein $R^1$ represents a straight-chain alkyl group having 9 to 17 carbon atoms and $R^2$ represents an acyl group having 11 to 24 carbon atoms which may contain at least one hydroxyl group or unsaturated bond to the keratin fiber by adhesion, coating or impregnation.

2. A method for improving the strength of keratin fiber according to claim 1, wherein in the formula (I), $R^1$ represents a straight-chain alkyl group having 9 to 17 carbon atoms and $R^2$ represents a saturated acyl group having 11 to 24 carbon atoms.

3. A method for improving the strength of keratin fiber according to claim 1, wherein in the formula (I), $R^1$ represents a $C_{13}H_{27}$, $C_{15}H_{31}$ or $C_{17}H_{35}$ group and $R^2$ represents an acyl group presented by any one of the following formulas (II) to (VII):

(III)

(IV)

(V)

(VI)

(VII)

wherein $R^3$ represents a hydrogen atom or a saturated alkyl group having 11 to 21 carbon atoms.

4. A method for improving the strength of keratin fiber according to claim 3, wherein in the formulas (II) to (VII), $R^3$ represents a $C_{11}H_{23}$, $C_{13}H_{27}$, $C_{15}H_{31}$ or $C_{17}H_{35}$ group.

5. A method for improving the strength of keratin fiber according to claim 1, wherein $R^2$ represents an acetyl, oleoyl, linoleoyl or linolenoyl group.

6. A method for improving the strength of keratin fiber according to claim 1, wherein the keratin fiber strengthening agent further comprises a cosmetically acceptable raw material.

7. A method for improving the strength of keratin fiber according to claim 6, wherein the cosmetically acceptable raw material comprises at least one material selected from the group consisting of oil components, lipids, sterols, lower or polyhydric alcohols and surfactants.

* * * * *